United States Patent [19]

Hall et al.

[11] Patent Number: 5,214,225
[45] Date of Patent: May 25, 1993

[54] DEHYDROGENATION PROCESS WITH IMPROVED HEAT RECOVERY

[76] Inventors: Stephen G. Hall, 12423 Carraige Hill, Houston, Tex. 77077; Robert B. Armstrong, 1058 Shillington Dr., Katy, Tex. 77450

[21] Appl. No.: 803,274
[22] Filed: Dec. 5, 1991
[51] Int. Cl.$^5$ ............................................. C07C 5/333
[52] U.S. Cl. .................................. 585/654; 585/658; 585/910
[58] Field of Search ..................... 585/658, 910, 654

[56] References Cited

U.S. PATENT DOCUMENTS

| | | | |
|---|---|---|---|
| 4,381,417 | 4/1983 | Vora et al. | 585/655 |
| 4,551,235 | 11/1985 | Carson | 208/100 |
| 4,581,339 | 4/1986 | Bhatt et al. | 502/38 |
| 4,806,624 | 2/1989 | Herber et al. | 585/440 |

Primary Examiner—Asok Pal
Assistant Examiner—P. Achutamurthy

[57] ABSTRACT

A process for making ethylenically unsaturated hydrocarbons from a saturated $C_3$–$C_5$ hydrocarbon feed with improved heat recovery. The feed is partially vaporized against hot discharge gases from product compressors, completely vaporized with low pressure steam and preheated against hot reactor effluent, before being heated by a process heater to reaction temperature and catalytically dehydrogenated in an adiabatic reactor. The process is controlled by regulating the low pressure steam supplied to the vaporizer, the heat input to the process heater, and cooling water flow to the process coolers.

12 Claims, 3 Drawing Sheets

DEHYDROGENATION PROCESS WITH IMPROVED HEAT RECOVERY

FIELD OF THE INVENTION

The present invention relates to a process for making ethylenically unsaturated hydrocarbons from a saturated $C_3$-$C_5$ hydrocarbon feed, and particularly to improvements in heat recovery in the process.

BACKGROUND OF THE INVENTION

The production of olefins from $C_3$-$C_5$ hydrocarbons is well known. The technology for producing olefins is available commercially from several sources, such as, for example, the Catofin/Catadiene process, the UOP Oleflex process, and the like. The processes typically involve selective catalytic dehydrogenation of a saturated hydrocarbon stream at elevated temperature. The primary differences between the commercially available technologies are generally in the configuration and operation of the dehydrogenation reactor, but each generally requires heating the hydrocarbon feed to the reactor and cooling the olefin-rich effluent from the reactor. Various approaches to recovering heat from the reactor effluent have included the production of steam and heat exchange with the feed. Even with these attempts at heat recovery, it has been necessary to provide additional heat for the hydrocarbon feed stream and cooling water for further cooling of the effluent stream. The shortcomings of the prior art heat recovery efforts are manifested in excessive cooling water, fuel and steam import requirements.

A typical prior art catalytic dehydrogenation unit design is schematically illustrated in FIG. 1. A feed stream 10 comprising mainly $C_3$-$C_5$ saturated hydrocarbons at ambient temperature is heated in a low pressure steam heat exchanger 12 to produce a vaporized feed stream 14. The vaporized feed stream 14 is heated against hot reactor effluent in exchanger 16 to produce a partially heated feed stream 18 which is heated to reaction temperature in a fired preheating furnace 20 to produce a hot feed stream 22 for the reactor 24.

The reactor 24 is typically an adiabatic, fixed-bed catalytic dehydrogenation reactor in which the saturated hydrocarbons in the feed are dehydrogenated to produce an olefin-rich stream 26. Catalyst regeneration is effected cyclically by using parallel reactors which are alternately taken off stream for regeneration, or continuously using reactors operated in a stacked series with continuous catalyst withdrawal for regeneration and recycle. Regardless, conversion to the desired olefin product is primarily controlled by reactor pressure and temperature. Because olefin yield is enhanced by lower pressures, the reactor 24 is typically operated at approximately atmospheric or subatmospheric pressure.

The hot effluent stream 26 is typically used to generate steam in exchanger 28. Furnace 20 flue gases, along with reactor regeneration gases can also be used for waste heat recovery for steam production. A partially cooled product stream 30 is supplied as the hot-side fluid to process heat exchanger 16 and further cooled in cooler 32 to a suitable temperature for compression. The cooler 32 can be an air cooler, but usually uses water, typically supplied from a recirculating cooling tower, as the heat exchange medium.

Because it is necessary to avoid excessive temperatures in the compression of the product stream to enhance compressor efficiency, compression is typically effected with a plurality of staged compressors 34, 36, 38 using intercoolers 40, 42 in series so that each compressor discharge has a temperature below about 260° F. and each compressor suction has a temperature of about 90°-125° F., although care is usually taken to ensure that the product is maintained in a gaseous phase. If desired, any condensate formed, for example, in the intercooler 42, can be removed using a separator (not shown) which is conventional for this purpose. An aftercooler 44, cools the high pressure product stream 46 to the desired temperature for subsequent finishing in section 48, typically including absorption, stripping and stabilization, to produce fuel gas stream 50 and an olefin-rich product stream 52.

SUMMARY OF THE INVENTION

The present invention resides in the discovery of improvements to heat recovery in the catalytic dehydrogenation process. The application of this discovery obtains reduced steam requirements and reduced cooling water consumption. It has been discovered that the saturated hydrocarbon feed can be preheated and partially vaporized against the process, and operability can be maintained by completing the final feed vaporization in a low pressure steam heater. A feed/compressor gas exchanger can be placed in the discharge of one or more of the compressor stages to achieve improved energy recovery.

Accordingly, the present invention provides a process for making ethylenically unsaturated hydrocarbons from a feed stream comprising saturated $C_3$-$C_5$ hydrocarbons. The process includes the following steps:

(a) passing the saturated $C_3$-$C_5$ hydrocarbons-containing feed stream in heat exchange with a hot process compressor discharge to partially vaporize the feed and at least partially cool the compressor discharge;
(b) passing the partially vaporized feed in heat exchange with low pressure steam to completely vaporize the feed;
(c) passing the vaporized feed in heat exchange with a hot product stream to form a partially preheated feed stream;
(d) passing the partially preheated feed stream through a preheating furnace to heat the feed stream to reaction temperature;
(e) contacting the feed with a dehydrogenation catalyst at reaction temperature to form ethylenically unsaturated hydrocarbons comprising the hot product stream;
(f) partially cooling the hot product stream before using the hot product stream in said heat exchange with said vaporized feed stream;
(g) after said heat exchange with the vaporized feed, passing the partially cooled product stream in heat exchange with cooling water to form a cooled, low pressure product stream;
(h) compressing the low pressure product stream to form the hot compressor discharge for said heat exchange with said feed; and
(i) passing the partially cooled compressor discharge in heat exchange with cooling water to form a cooled, high pressure ethylenically unsaturated hydrocarbon product stream.

DESCRIPTION OF THE INVENTION

Figure 1:
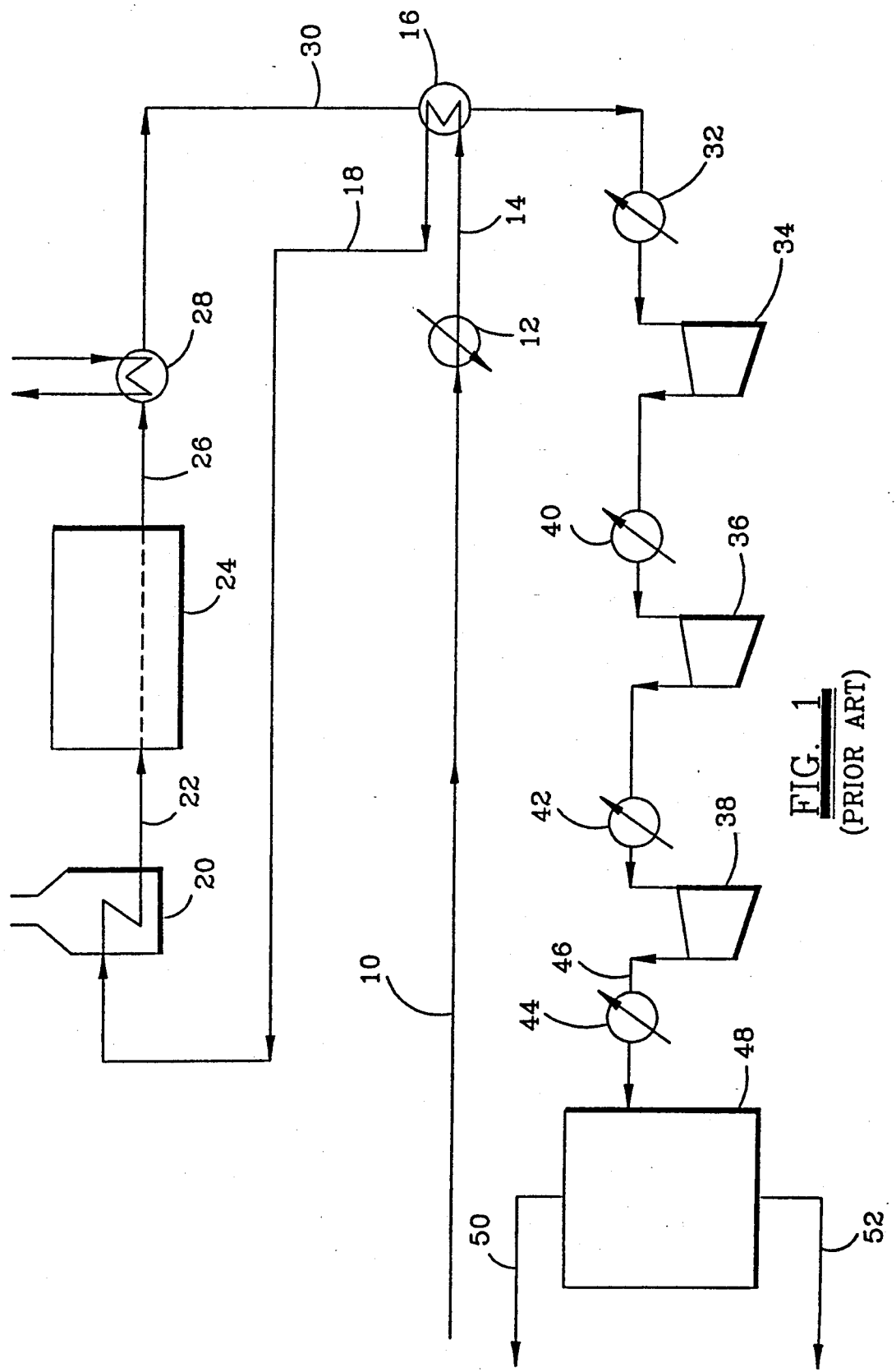
FIG. 1 is a schematic illustration of a prior art catalytic dehydrogenation unit as described above.
Figure 2:
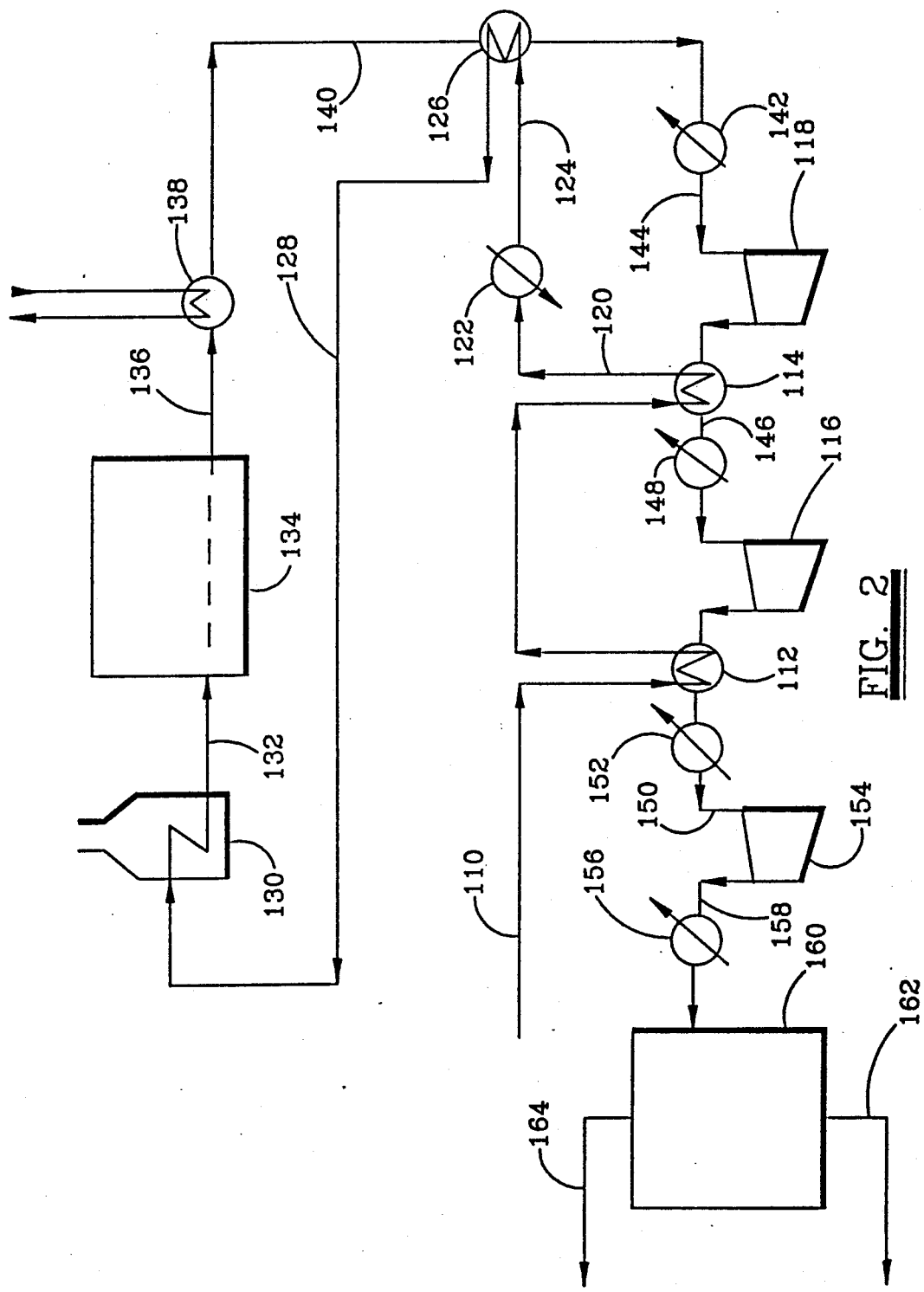
FIG. 2 is a schematic illustration of a catalytic dehydrogenation process with improved heat recovery in accordance with an embodiment of the present invention. Saturated hydrocarbon feed stream 110 at 60° F. is heated in series in process exchangers 112 and 114 using hot compressor discharge from secondary and primary stage compressors 116 and 118, respectively, to obtain a partially vaporized feed stream 120 at a temperature of about 118° to 119° F. The partially vaporized feed stream 120 is completely vaporized and heated in heat exchanger 122 with steam at about 170° F. to obtain a superheated feed stream 124 at a temperature of about 135° F. The vaporized feed stream 124 is heated against hot reactor effluent in process heat exchanger 126 to produce a partially heated feed stream 128 at about 430° to 440° F. which is heated to reaction temperature in preheating furnace 130 to produce a hot feed stream 132 for reactor 134. The saturated hydrocarbons in the feed stream are at least partially converted to ethylenically unsaturated hydrocarbons in olefin-rich stream 136. The hot effluent stream 136 is used to generate steam and/or heated boiler feed water in exchanger 138. A partially cooled product stream 140 at about 570° F. is supplied as the hot-side fluid to the exchanger 126 and subsequently cooled from about 350° F. in cooler 142 with water to form a compressor section feed stream 144 at a temperature of about 110° F. The stream 144 is compressed in primary stage compressor 118 and discharged to exchanger 114 at a temperature of about 230° F. to form a partially intercooled stream 146 having a temperature of about 142° F. Stream 146 is then cooled to a temperature of about 105° F. in water exchanger 148. The effluent product from exchanger 148 is then compressed in second stage compressor 116 and cooled from a temperature of about 219° F. in exchanger 112 to form a partially cooled second stage product stream 150 having a temperature of about 105° F. Water exchanger 152 is provided in line 150 for optional cooling if the exchanger 112 does not sufficiently cool stream 150. A third stage compressor 154 compresses the product stream 150 to about 180 psia and 247° F. and aftercooler 156 is supplied with water to produce a crude product stream 158 at a temperature of about 105° F. The crude product stream 158 is subsequently processed in absorption, stripping and stabilization section 160 to obtain olefinrich product stream 162 and fuel gas stream 164.
Figure 3:
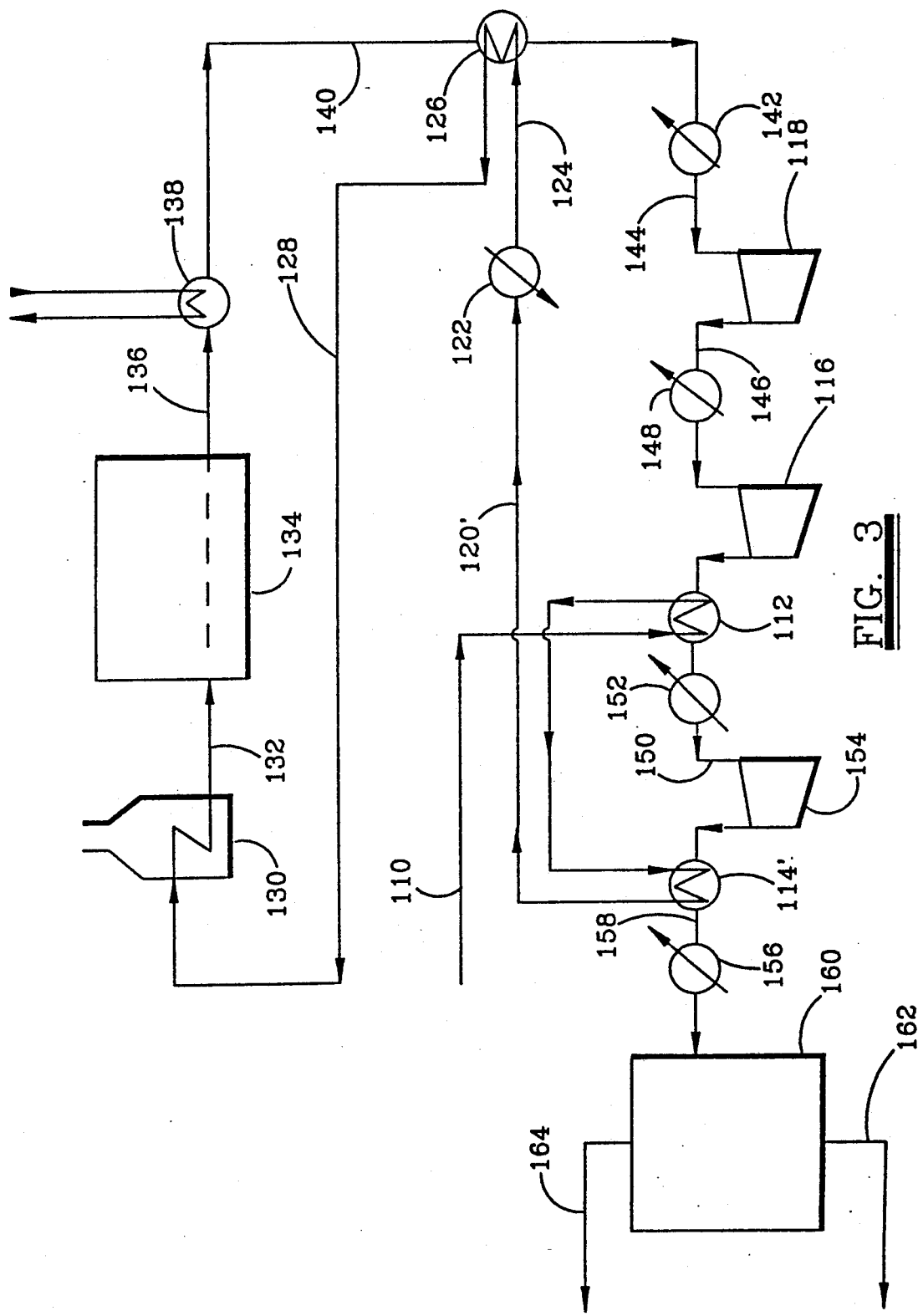
FIG. 3 schematically illustrates a further embodiment of the invention wherein the exchanger 114' is disposed in the third stage compressor 154 discharge, instead of the first stage compressor discharge 146. A partially vaporized stream 120' at about 118° F. is supplied to the exchanger 122. The remaining, like-numbered components of the process are functionally equivalent with those of FIG. 2.

The present invention is generally applicable to processes for the catalytic dehydrogenation of saturated hydrocarbon feed streams. The feed stream chiefly comprises $C_3$–$C_5$ hydrocarbons, such as, for example, propane, isobutane, normal butane, pentane, 2-methylbutane, and the like, generally a mixture thereof. A relatively minor proportion of unsaturated hydrocarbons, such as isobutene and 1-butene, typically as much as about 5 weight percent, may also be present in the feed stream, and the term "saturated" is intended to include such feed streams when used in reference thereto. The feed stream composition can also contain relatively minor amounts of methane, ethane and inert compounds such as nitrogen but is generally free of oxygen, sulfur and other compounds which can adversely affect the catalytic dehydrogenation. The saturated hydrocarbon feed stream composition depends on availability and the desired product. For example, where propylene is the desired product, the feed stream generally has a higher propane content, whereas a feed stream having a higher isobutane content is used where isobutylene is the desired product.

Conventional catalytic dehydrogenation reactors are employed for converting the saturated hydrocarbon feed stream into an olefin-rich product stream. These are generally adiabatic, fixed-bed reactors, although fluid bed reactors are sometimes employed. The reactors are typically operated at a temperature of from about 800° F. to about 1200° F. and a pressure from about 0.1 to about 2 atmospheres. The conversion to the desired product is determined largely by the pressure and temperature selection, in addition to feed composition.

In the present invention, the saturated hydrocarbon feed stream is preheated and partially vaporized by heat exchange against the hot compressor discharge stream(s) obtained by compression of the product olefin-rich stream; vaporization is completed in a low pressure steam heat exchanger; and the feed stream is further heated in heat exchange against the reactor product effluent. In the initial partial vaporization of the cold feed against the hot compressor discharge gases, enough heat is supplied to heat the cold feed and partially vaporize the feed stream. The compressor discharge gases are similarly cooled against the feed stream, and in an intercooler positioned between the plural compressor stages in series in one or more compressor discharges, or an aftercooler down stream from the final compressor stage. In general, the compression of the product olefin stream is effected in a plurality of intercooled stages to avoid excessively high temperatures in the product gas which would otherwise cause compressor efficiency to drop and power requirements to increase. Thus, the intercoolers are employed to sufficiently cool the hot compressor discharge so that excessive temperatures during compression in each subsequent stage are avoided. Preferably, the temperature in the discharge is maintained below about 300° F., more preferably below about 275° F. The intercoolers desirably cool the discharge as much as possible, but temperatures in the range of from about 90° F. to about 120° F. are generally achieved as a practical matter since cooling water is typically employed as the cooling medium.

It has been found that the feed stream can be heated and partially vaporized by heat exchange with the hot compressor discharge gases. For operability and to prevent excessive fouling, however, the final 5 to 10 percent of vaporization, at a minimum, is effected in a low pressure steam heater to avoid excessive temperature differences during the final vaporization. Operability is generally enhanced by supplying the low pressure steam at a pressure and rate sufficient to obtain a desired superheated vapor feed stream. Thus, heating of the cold feed to its boiling point and from about 50 to about 95 percent of the vaporization can be effected by heat exchange of the feed against the hot compressor discharge gases, preferably from about 65 to about 90 percent of the vaporization. Typically, vaporization of the feed stream occurs at approximately 110° F. to 120° F., although the specific temperature depends on the composition of the feed stream and the pressure. Thus, a substantial proportion of the feed stream can be vaporized even though the resultant temperature of the feed stream may drop due to expansion of the feed stream gases due to the pressure differential across the heat exchangers.

Preferably, the feed stream is partially vaporized by heat exchange with more than one compressor stage discharge. For example, the feed stream can be partially vaporized by heat exchange against the compressor discharge gases from the primary and intermediate stages; intermediate and final stages; primary and final stages; primary, intermediate and final stages; and like combinations. In general, higher heat transfer coefficients and higher enthalpy are obtained when a higher pressure gas discharge is used, e.g. the final stage discharge will provide more heat for vaporization of the feed than, say, the primary stage compressor, but as a practical matter, the cost of the heat exchange equipment is generally lower when the heat exchanger is placed in a lower pressure service, as in the discharge from the primary and/or intermediate stage compressors. Thus, the selection of a location for each heat exchanger in the compressor discharge gases depends on the specific conditions of the process and must be evaluated on a case-by-case basis.

In a preferred embodiment, the feed is partially vaporized by heat exchange against a plurality of compressor discharges. The bulk of the feed stream is routed through each heat exchanger, appropriately sized and located in a compressor discharge according to engineering principles, without control of the flow rate or pressure of the feed stream therethrough. Any further cooling of the compressor discharge prior to subsequent compression or other processing is effected by supplying cooling water to a cooler positioned in the respective compressor discharger downstream from the indirect feed stream heat exchanger. The cooling water is generally supplied at a rate and temperature sufficient to obtain a low enough temperature in the compressor discharge for subsequent compression or other processing as desired. In other words, the temperature to which each compressor discharge stage is cooled is controlled by regulating the cooling water supply.

Similarly, the heating and vaporization of the feed stream is effected by heat exchange against the hot compressor discharges by designing the heat exchangers so that passing the bulk of the feed stream through the heat exchangers obtains only partial vaporization. Then, the final vaporization of the feed stream is effected by controlling the steam pressure and/or rate to the low pressure steam heat exchanger so that the vaporized feed stream is obtained at a predetermined temperature. The temperature of the vaporized feed stream from the low pressure steam exchanger preferably has a certain amount of superheat to ensure complete vaporization so that there will be no vaporization occurring in the heat exchange against the product stream. Preferably, the temperature of the feed stream leaving the low pressure steam heat exchanger is on the order of from about 130° F. to about 150° F., although the precise temperature, of course, depends on the composition and pressure of the feed stream and the temperature of the low pressure steam supply.

The final vaporization of the feed stream is preferably effected in a low pressure steam heat exchanger. Low pressure steam, preferably subatmospheric steam, is supplied to the low pressure heat exchanger to effect up to the final 5 to 50 percent of feed vaporization, more preferably the final 10 to 35 percent of feed vaporization. The maximum temperature difference between the feed stream and the low pressure steam ($\Delta T_{max}$) should not exceed 100° F., and preferably does not exceed 50° F. Where $\Delta T_{max}$ is too high during the vaporization of the last 5 to 10 percent of the feed stream, excessive fouling can occur. Thus, even though the feed stream could be completely vaporized against the hot product compressor discharge gases (or even against the hot reactor effluent), it is preferred to employ a low pressure steam exchanger to complete the final feed vaporization to minimize exchanger fouling and for operability and control purposes. On the other hand, the more vaporization which is done in the low pressure steam heat exchanger, the less benefit there will be from the use of the present invention. The steam exchanger is also desirably present in the process for use at higher heat duty for start up and maintenance purposes, and in other situations, when it is necessary to bypass the compressor discharge exchanger(s).

The process heat exchanger is designed for preheating the bulk feed stream to the greatest extent economically possible. Thus, the heat exchanger is designed to obtain an exit $\Delta T$ (the temperature difference between the hot side fluid supplied to the exchanger and the heated cold side fluid leaving the exchanger) of from about 100° to about 150° F. The preheated feed stream vapor generally has a temperature of from about 400° to about 500° F., depending on the feed composition and pressure, as is known in the art. More heating than this is generally not economical because of the excessive heat exchanger cost and pressure drops. The reaction temperature of the feed stream is controlled by controlling the amount of heat supplied to the preheating furnace. Thus, the bulk of the feed stream is routed through the process heat exchanger without regulation of flow rate or bypass or pressure, and the amount of heat input to the furnace is controlled responsive to the desired reactor inlet temperature used as a set point. The reactor inlet temperature is, of course, dictated by the desired product equilibrium as described above.

Before exchanging heat with the feed stream, the reactor effluent is preferably used to heat boiler feed water and/or to generate steam. In general, the boiler feed water is supplied to the heat exchanger located in the product effluent line to extract sensible heat from the product stream for heating the boiler feed water and/or generating steam using the conventional boiler feed water heater/steam generation operated in accordance with conventional techniques. Typically, the product stream partially cooled by the boiler feed water exchanger/steam generator is in the temperature of from about 500° to about 600° F. for supply to the process heat exchanger. Following heat exchange with the feed stream, the product stream is cooled, for example, by air or cooling water (or by partially vaporizing the feed stream in heat exchange), to the desired temperature for compression in the primary compressor stage.

The foregoing description of the invention is illustrative and explanatory, and not to be considered as a limitation to the invention. Various modifications of and variations to the illustrative embodiments described above will occur to those skilled in the art in view of the foregoing disclosure of the invention. It is intended that all such variations and modifications within the scope or spirit of the appended claims be embraced thereby.

What is claimed is:

1. In a process for making ethylenically unsaturated hydrocarbons from a saturated $C_3$–$C_5$ hydrocarbon feed stream wherein the feed is passed in heat exchange with steam to completely vaporize the feed; the completely vaporized feed is passed in heat exchange with a hot product stream to form a partially preheated feed stream; the partially preheated feed stream is heated to reaction temperature, the heated feed stream is contacted with a dehydrogenation catalyst at reaction temperature to form ethylenically unsaturated hydrocarbons comprising a hot product stream, the hot product stream is partially cooled before using the hot product stream in said heat exchange with the completely vaporized feed stream; the partially cooled product stream is further cooled to form a cooled, low pressure product stream; and the cooled low pressure product stream is compressed to form a hot compressor discharge stream the improvement which comprises the steps of:
   (i) passing the saturated $C_3$–$C_5$ hydrocarbon feed stream in heat exchange with the hot compressor discharge stream to heat and partially vaporize the feed stream and to partially cool the hot compressor discharge stream; and
   (ii) passing the partially vaporized feed stream from step (i) in heat exchange with low pressure steam to complete vaporization of the partially vaporized hydrocarbon feed stream.

2. The improved process of claim 1, wherein the partially vaporized feed stream from step (i) has a temperature from about 110° F. to about 130° F.

3. The improved process of claim 1, wherein the vaporized feed stream from step (b) has a temperature from about 130° F. to about 150° F.

4. The improved process of claim 1, wherein the final 5 to 50 percent of the feed vaporization is effected in step (ii).

5. The improved process of claim 1, wherein the heat transfer in step (ii) is controlled by regulating the low pressure steam to obtain the vaporized feed at a predetermined temperature.

6. In a process for making ethylenically unsaturated hydrocarbons from a saturated $C_3$–$C_5$ hydrocarbon feed stream wherein the feed stream is passed in heat exchange with steam to completely vaporize the feed; the completely vaporized feed is passed in heat exchange with a hot product stream to form a partially preheated feed stream; the partially preheated feed stream is heated to reaction temperature; the heated feed stream is contacted with a dehydrogenation catalyst at reaction temperature to form ethylenically unsaturated hydrocarbons comprising a hot product stream; the hot product stream is partially cooled before using the hot product stream in said heat exchange with the completely vaporized feed stream; the partially cooled product stream is further cooled to form a cooled, low pressure product stream and the cooled, low pressure product stream is compressed in a plurality of compressors in series to form a plurality of intermediate hot compressor discharge streams and a hot, high pressure product stream in series, the improvement which comprises the steps of:
   (i) successively passing the saturated $C_3$–$C_5$ hydrocarbon feed stream in heat exchange with the plurality of intermediate hot compressor discharge streams or at least one of said plurality of intermediate hot discharge streams and the hot, high pressure product stream to heat the feed stream to form a partially vaporized feed stream at a temperature of about 110° F. to about 130° F. and to partially cool the plurality of intermediate hot compressor discharge streams or the at least one of said plurality of hot discharge streams and the hot product stream; and
   (ii) passing the partially vaporized feed stream through a heat exchanger in heat exchange with low pressure steam supplied at a pressure and rate effective to obtain a completely vaporized feed stream at a predetermined temperature between about 130° F. and about 150° F.

7. The improved process of claim 6 wherein said partially vaporized feed stream is comprised of from about 5 to about 50 percent liquid.

8. The improved process of claim 6 where in step (i) the hydrocarbon feed stream is subjected to heat exchange in series with at least two of said plurality of intermediate hot compressor discharge streams to partially cool said discharge streams.

9. The improved process of claim 8 wherein each of the partially cooled intermediate discharge streams is further cooled by heat exchange with cooling water.

10. The improved process of claim 9, wherein the heat transfer is controlled by regulating the rate of cooling water supply for cooling each of the discharge streams to a predetermined temperature.

11. The improved process of claim 9, wherein the product stream has an enriched content of propylene, butene, isobutylene pentene, methylbutene or a mixture thereof.

12. The improved process of claim 9, wherein the product stream has an enriched content of diene.

* * * * *